US011241155B2

(12) United States Patent
Chen et al.

(10) Patent No.: US 11,241,155 B2
(45) Date of Patent: Feb. 8, 2022

(54) OPTICAL COHERENCE TOMOGRAPHY DEVICE FOR CHARACTERIZATION OF ATHEROSCLEROSIS WITH A 1.7 MICRON SWEPT LASER SOURCE

(71) Applicant: The Regents of the University of California, Oakland, CA (US)

(72) Inventors: Zhongping Chen, Irvine, CA (US); Yan Li, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 354 days.

(21) Appl. No.: 15/878,762

(22) Filed: Jan. 24, 2018

(65) Prior Publication Data
US 2018/0214023 A1 Aug. 2, 2018

Related U.S. Application Data

(60) Provisional application No. 62/451,210, filed on Jan. 27, 2017.

(51) Int. Cl.
*A61B 5/00* (2006.01)
*A61B 8/08* (2006.01)
(Continued)

(52) U.S. Cl.
CPC .......... *A61B 5/0035* (2013.01); *A61B 5/0066* (2013.01); *A61B 5/02028* (2013.01);
(Continued)

(58) Field of Classification Search
CPC ... A61B 5/0075; A61B 5/0095; A61B 5/0071; A61B 5/0035; A61B 5/0066;
(Continued)

(56) References Cited

U.S. PATENT DOCUMENTS 9,777,053 B2 * 10/2017 Yun ...................... A61B 5/0095
2009/0021724 A1 * 1/2009 Mahadevan-Jansen ..................... A61B 5/445
356/73

(Continued)

OTHER PUBLICATIONS

Piao, Z. et al. High speed intravascular photoacoustic imaging with fast optical parametric oscillator laser at 1.7 um. Applied physics letters 107, 083701, doi: 10.1063/1.4929584 (2015). (Year: 2015).*

(Continued)

*Primary Examiner* — Christopher Koharski
*Assistant Examiner* — Kaitlyn E Selmer
(74) *Attorney, Agent, or Firm* — Nguyen Tarbet LLC

(57) ABSTRACT

An OCT system with a swept light source centered around 1.7 μm for identifying atherosclerotic plaque and visualization of large lipid pool is provided. Advantages for using the 1.7 μm swept source laser include higher contrast between lipid and normal tissue and deeper penetration of the optical signals from the 1.7 μm swept source laser into the tissue. With deeper penetration into the tissue, more structural information from deep within the tissue is obtained. The present invention also features multimodality imaging systems that integrate additional imaging systems into the OCT system at 1.7 μm. As an example, an integrated 1.3 μm and 1.7 μm OCT system is provided which simultaneously generates OCT images using both the OCT systems which are used to characterize and differentiate the types of tissue.

10 Claims, 11 Drawing Sheets

(51) Int. Cl.
*A61B 5/02* (2006.01)
*A61B 8/12* (2006.01)

(52) U.S. Cl.
CPC ............... *A61B 8/12* (2013.01); *A61B 8/485* (2013.01); *A61B 8/5261* (2013.01); *A61B 5/0071* (2013.01); *A61B 5/0075* (2013.01); *A61B 5/0095* (2013.01)

(58) Field of Classification Search
CPC ....... A61B 5/02028; A61B 8/485; A61B 8/12; A61B 8/5261
See application file for complete search history.

(56) References Cited

U.S. PATENT DOCUMENTS

| | | | |
|---|---|---|---|
| 2009/0021746 A1* | 1/2009 | Toida ................. | G01N 21/6428 356/484 |
| 2011/0098572 A1* | 4/2011 | Chen ................... | A61B 5/0095 |
| 2016/0242737 A1* | 8/2016 | Zhou .................... | A61B 5/0084 |
| 2017/0020387 A1* | 1/2017 | Fingler ................ | A61B 3/0025 |

OTHER PUBLICATIONS

Zhu, J. et al. Imaging and characterizing shear wave and shear modulus under orthogonal acoustic radiation force excitation using OCT Doppler variance method. Opt Lett 40, 2099-2102, doi: 10.1364/Ol.40.002099. (2015) (Year: 2015).*

Piao et al. High speed intravascular photoacoustic imaging with fast optical parametric oscillator laser at 1.7 micrometers, 2015 (Year: 2015).*

Abran M, et al., "Validating a bimodal intravascular ultrasound (IVUS) and near-infrared fluorescence (NIRF) catheter for atherosclerotic plaque detection in rabbits," Biomed Opt Express. Sep. 1, 20154 ;6(10):3989-99. doi: 10.1364/Boe.6.003989 (2015).

Ambrose, J.A., et al., "Angiographic progression of coronary artery disease and the development of myocardial infarction.J Am Coll Cardiol," 1988;12:56-62.

Falk E., Shah P. K., and Fuster V., "Coronary Plaque Disruption," Circulation 92, 657-671 (1995).

Finn A.V., Nakano M., Narula J., Kolodgie F. D., and Virmani R., "Concept of Vulnerable/Unstable Plaque," ArterosclThrom Vas 30, 1282-1292 (2010). [doi: 10.1161/ATVBAHA. 108.179739].

Fujimoto J et al., "High resolution in vivo intra-arterial imaging with optical coherence tomography," Heart. 1999; 82(2):128-133.

Jing, J. C., Chou, L. D., Su, E. C., Wong, B. J. F. & Chen, Z (2015). P. Anatomically correct visualization of the human upper airway using a high-speed long range optical coherence tomography system with an integrated positioning sensor. Sci Rep—Uk 6, doi:Artn 3944310.1038/Srep39443 (2016).

Li, J. et al. Integrated IVUS-OCT for real-time imaging of coronary atherosclerosis. JACC. Cardiovascular imaging 7, 101-103, doi:10.1016/j.jcmg.2013.07.012 (2014).

Li, J. W. et al. Ultrafast optical-ultrasonic system and miniaturized catheter for imaging and characterizing atherosclerotic plaques in vivo. Sci Rep—Uk 5, doi:Artn 1840610.1038/Srep18406 (2015).

Li, Y. et al. Fully integrated optical coherence tomography, ultrasound, and indocyanine green-based fluorescence tri-modality system for intravascular imaging. Biomedical optics express 8, 1036-1044, doi:10.1364/BOE.8.001036 (2017).

Li, Y. et al. High-speed intravascular spectroscopic photoacoustic imaging at 1000 A-lines per second with a 0.9-mm diameter catheter. J Biomed Opt 20, doi:Artn 06500610.1117/1.Jbo.20.6.065006 (2015).

Naghav, M. et al., "From vulnerable plaque to vulnerable patient: a call for new definitions and risk assessment strategies: Part II," Circulation 108(15), 1772-1778 (2003).

Piao, Z. et al. High speed intravascular photoacoustic imaging with fast optical parametric oscillator laser at 1.7 um. Applied physics letters 107, 083701, doi:10.1063/1.4929584 (2015).

Tearney G J et al., "Quantification of macrophage content in atherosclerotic plaques byoptical coherence tomography," Circulation 107(1), 113-119 (2003).

Tearney GJ, et al. Three-dimensional coronary artery microscopy by intracoronary optical frequency domain imaging. J Am Coll CardiolImg. 2008;1:752-61.

Tearney, G. J. et al. In vivo endoscopic optical biopsy with optical coherence tomography. Science 276,2037-2039, doi:DOI 10 1126/science.276.5321.2037 (1997).

Tsai, C. L., Chen, J. C. & Wang, W. J. Near-infrared Absorption Property of Biological Soft Tissue Constituents,. Journal of Medical and Biological Engineering 21, 7-14 (2001).

Yabushita, H., et al. Characterization of human atherosclerosis by optical coherence tomography. Circulation. 2002;106: 1640-1645.

Yin, J. et al. Integrated intravascular optical coherence tomography ultrasound imaging system. J Biomed Opt 15, 010512, doi:10.1117/1.3308642 (2010).

Zhu, J. et al. 3D mapping of elastic modulus using shear wave optical micro-elastography. Sci Rep—Uk 6, doi:Artn 3549910.1038/Srep35499 (2016).

Zhu, J. et al. Imaging and characterizing shear wave and shear modulus under orthogonal acoustic radiation force excitation using OCT Doppler variance method. Opt Lett 40, 2099-2102, doi:10.1364/Ol.40.002099. (2015).

* cited by examiner

OPTICAL COHERENCE TOMOGRAPHY DEVICE FOR CHARACTERIZATION OF ATHEROSCLEROSIS WITH A 1.7 MICRON SWEPT LASER SOURCE

CROSS REFERENCE

This application claims priority to U.S. patent application No. 62/451,210, filed Jan. 27, 2017, the specification(s) of which is/are incorporated herein in their entirety by reference.

GOVERNMENT SUPPORT

This invention was made with government support under Grant No. R01HL-125084 and R01HL-127271, awarded by NIH. The government has certain rights in the invention.

FIELD OF THE INVENTION

The present invention relates to the field of intravascular optical coherence tomography ("OCT") for characterization of atherosclerosis.

BACKGROUND OF THE INVENTION

Cardiovascular disease is the leading cause of death in developed countries and ruptured atherosclerotic plaques are the main cause of acute coronary events. Identifying plaque type plays an important role in choosing proper interventional techniques. Therefore, accurate assessment of plaque is critical in the clinic. According to clinical studies, there are three characteristics of vulnerable plaques which are used as the criteria to estimate the presence of vulnerable plaques, (i) large lipid pool, (ii) thin fibrous cap, and (iii) major inflammatory reaction. Various imaging technologies have been developed to detect vulnerable plaques with the hope of guiding patient management and monitoring response to intervention. For example, intravascular optical coherence tomography (IVOCT) offers a superior spatial resolution of ~15 µm, which has enabled the detection of micrometer-scale features of atherosclerosis.

In the clinic, the IVOCT device, based on a swept source laser with a center wavelength 1.3 µm, is often used for identifying the thin fibrous cap. However, limited by depth penetration of conventional IVOCT devices, it is difficult to visualize the large lipid pool. Therefore, intravascular ultrasound (IVUS) imaging both the lumen geometry and structure of the arterial wall (with an imaging depth of ~7 mm and a resolution of ~150 µm) are often applied in order to identify large lipid pools.

SUMMARY OF THE INVENTION

The present invention includes an optical coherence tomography (OCT) system having a swept laser source with a wavelength in a lipid absorption spectrum, effective for acquiring structural and chemical information of a tissue. In some aspects, the lipid absorption spectrum ranges from about 1.65 to 1.8, and an exemplary wavelength is about 1.7 µm. One of the unique and inventive technical features of the present invention is the application of a 1.7 µm swept source laser in the OCT system for identification of atherosclerosis. Without wishing to limit the invention to any theory or mechanism, it is believed that the technical feature of the present invention advantageously provides for higher sensitivity and increased depth penetration. As an example, based on the lipid absorption spectrum, 1.7 µm wavelength excitation leads to increased sensitivity, providing more obvious contrast between lipid and normal tissue. In addition, the OCT images with long wavelength will obtain large depth penetration, which enable the possibility of visualization of the entire large lipid pool. In this way, the proposed OCT system allows identification of the morphology of atherosclerotic plaque and has the potential to detect its chemical composition. OCT system discussed in this invention, also include functional OCT system, such as spectroscopic OCT, Doppler OCT, and polarization sensitive OCT. None of the presently known prior references or work has the unique inventive technical feature of the present invention.

Blood and water have a strong absorption in the 1.7 µm region and typically, intravascular OCT is applied with water/blood/other liquids present, thus one of ordinary skill in the art may not use a 1.7 µm OCT system in intravascular imaging since it will result in decreased signal. However, the inventors have performed experiments which show the following unexpected result: the penetration depth of 1.7 µm system is higher than that of the 1.3 µm system even in the presence of water (discussed further below with reference to FIGS. 11A-F). Using the 1.7 µm system as opposed to the traditional 1.3 µm system, the inventors were able to readily differentiate plaque from normal tissue as shown in the images of atherosclerotic coronary arteries, as discussed further below with reference to FIG. 12. In addition, the present invention demonstrates an unexpected result that it is possible to use the 1.7 µm OCT system with components that are designed for 1.3 and/or 1.55 µm and still achieve high imaging quality.

In some aspects, a spectroscopic OCT may be applied if the molecular contrast is needed. However, the spatial resolution will be sacrificed by the usage of the spectroscopic OCT with high spectral resolution, and the technique suffers from high noise. To overcome this drawback, the present invention provides an integrated 1.3 µm/1.7 µm system in a single system to acquire 1.3 µm/1.7 µm intravascular OCT images simultaneously. This combined 1.3 µm/1.7 µm OCT system provides molecular contrast by calculating the ratio of OCT intensity at two wavelengths while maintaining the spatial resolution of the system. Surprisingly, the ratio of the OCT intensity at these two wavelengths may provide high molecular contrast of tissue, while maintaining high spatial resolution, including quantification of lipid types, collagen, and the like. Further still, in conventional spectroscopic OCT system, the sensitivity is limited by the scan range of the swept source laser of the OCT system. The combined 1.3 µm/1.7 µm intravascular OCT images can provide improved sensitivity for differentiating the different tissue components due to the usage of two scan ranges.

An optical coherence tomography ("OCT") system effective for acquiring structural and chemical information of a tissue is provided. The system may include at least one swept laser source ("laser source") having a wavelength in a lipid absorption spectrum, a first coupler, operatively connected to the laser source, configured to split an optical signal emitted by the laser source into a first optical signal and a second optical signal. The system may additionally include a first optical circulator operatively connected to the first coupler. The first optical circulator may include a first port, a second port, and a third port. The first optical signal may enter the first port and exit through the second port, whereupon exiting the second port, the first optical signal may be routed to a collimator before being reflected back to the second port via a reference mirror. The first optical signal may then exit the first optical circulator via the third port. The system may additionally include a second optical circulator operatively connected to the first coupler. The second optical circulator may include a fourth port, a fifth port, and a sixth port. The second optical signal may enter the fourth port and exit the fifth port, whereupon exiting the fifth port, the second optical signal may be routed to a probe operatively connected to the tissue. An interference signal may result from interactions between the second optical signal and the tissue, and the interference signal may re-enter the fifth port to exit through the sixth port. The system may additionally include a second coupler operatively connected to the third port and the sixth port, wherein the first optical signal and the interference signal comprise input to the second coupler. The second coupler may splits the first optical signal and the interference signal in a 50:50 split ratio. The system may additionally include a photodetector having a data acquisition board, configured to detect and record an output of the second coupler. The output of the second coupler may contain structural information describing the tissue, and wherein an output of the photodetector may be transmitted to an OCT device for imaging. The wavelength of the laser source may be centered between about 1.65-1.8 μm. The system may comprise a spectral domain OCT system employing a broadband light source centered at wavelengths between about 1.65-1.8 μm, and a spectral meter at a detection arm of the OCT system. One or more imaging systems or combinations thereof may be integrated into the OCT system to produce a multimodality imaging system. The one or more imaging systems may include an ultrasound ("US") imaging system, a fluorescence imaging system, an optical coherence elastography imaging system, a photoacoustic (PAT) imaging system, near-infrared spectroscopy imaging system, a fractional flow reserve (FFR) measurement system, a 1.3 μm swept source laser (1004) system, or combinations thereof.

An example method of producing an optical coherence tomography (OCT) image is provided. The method may include providing an OCT system (such as the OCT system disclosed above), and generating a first signal from a source signal of the laser source by reflecting a first portion of the source signal from a mirror positioned along a first path of the laser source. The method may additionally include generating a second signal by interfering a second portion of the source signal with a tissue positioned along a second path of the laser source, and coupling the first signal and the second signal to generate an image signal. The method may additionally include generating an optical coherence tomography (OCT) image based on the image signal, wherein the OCT image generated by coupling the first signal and the second signal contains structural information describing the tissue.

The method of claim may additionally include generating the first portion of the source signal by splitting the source signal at a first coupler positioned downstream of the laser source, directing the first portion of the source signal towards a first circulator and then towards the mirror. Herein, the first circulator may be positioned along the first path, and wherein the laser source may include a laser with center wavelength between about 1.65-1.8 μm. The method may additionally include generating the second portion of the source signal by splitting the source signal at the first coupler, directing the second portion of the source signal towards a second circulator, and then towards the tissue, the second circulator positioned along the second path. The method may additionally include transmitting the first signal from the mirror towards the first circulator and then towards a second coupler; and transmitting the second signal from the tissue towards the second circulator and then towards the second coupler. The first coupler may be a 90:10 coupler and the second coupler may be a 50:50 coupler, and each of the first circulator and the second circulator may be a three-port circulator each having three ports. The method may additionally include acquiring one or more of an ultrasound signal, a fluorescence signal, an optical coherence elastography (OCE) signal, and a photoacoustic signal from the tissue while generating the OCT image of the tissue using the swept laser source.

An example intravascular optical coherence tomography (IVOCT) system to detect thin fibrous cap of vulnerable plaque in a tissue is also provided. The system may include a swept laser source configured to generate an optical signal, the swept laser source having a center wavelength between about 1.65-1.8 μm. The system may additionally include a first coupler configured to direct 10% of the optical signal towards a mirror, and 90% of the optical signal towards the tissue. The system may additionally include a second coupler configured to receive a reflected signal from the mirror and an interference signal from the tissue and further configured to 50:50 split the reflected signal and the interference signal towards a photodetector. The system may additionally include a processor configured with computer readable instructions stored on non-transitory memory for: receiving a signal from the photodetector, the signal generated based on each of the reflected signal and the interference signal from a location of the tissue, and generating an OCT image based on the signal of the location the tissue, the signal originating from deep within the tissue and wherein the OCT images may include a high contrast image generated from deep within the tissue. The processor may include further instructions for: generating the signal along with one or more of an ultrasound imaging signal, a fluorescence imaging signal, an optical coherence elastography (OCE) signal, and a photoacoustic signal of the location of the tissue.

An integrated optical coherence tomography (OCT) system for differentiating plaque types is also provided. The system may include a first swept source laser ("first laser source") centered at a first wavelength configured to generate a first signal, and a second swept source laser ("second laser source") centered at a second wavelength different from the first wavelength configured to generate a second signal. The system may additionally include a wavelength division multiplexer (WDM) operatively coupled to each of the first laser source and the second laser source and configured to multiplex the first signal and the second signal to generate a third signal, and a collimator to collimate the third signal. The system may additionally include a first beam splitter configured to reflect a portion of the third signal towards a mirror and transmit a remaining portion of the third signal towards a sample, and a second beam splitter configured to separate the portion of third signal reflected from the mirror and a fourth signal generated from the sample towards a first photodetector and a second photodetector. The first photodetector may detect a portion of the fourth signal centered around the first wavelength and the second photodetector may simultaneously detect a remaining portion of the fourth signal centered around the second wavelength. Herein, the plaque types may be differentiated based on a ratio of outputs of the first photodetector centered at the first wavelength and the second photodetector centered at the second wavelength, which provides higher molecular contrast of tissue while maintaining high spatial resolution. The first wavelength may be centered between about 1.65-1.8 µm, and the second wavelength may be centered between about 1.2 to 1.4 µm. The integrated OCT system may be an integrated microscopic imaging system. The sample may be a tissue, and the first beam splitter may be configured to transmit the remaining portion of the third signal towards a scanner for scanning the tissue, and the integrated OCT system may be an integrated intravascular imaging system, A trigger signal from one or more of the first laser source and the second laser source may be applied as a main trigger signal to synchronize the integrated OCT system. A first OCT image may be generated based on a first output of the first photodetector centered at about 1.7 µm and a second OCT image may be generated based on a second output of the second photodetector centered at about 1.3 µm. One or more collagen, fibrous, fibro-fatty, calcium, and cholesterol may be identified based on a ratio of the first output and the second output for differentiating different plaque types.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which.

DETAILED DESCRIPTION OF THE INVENTION

Figure 1:
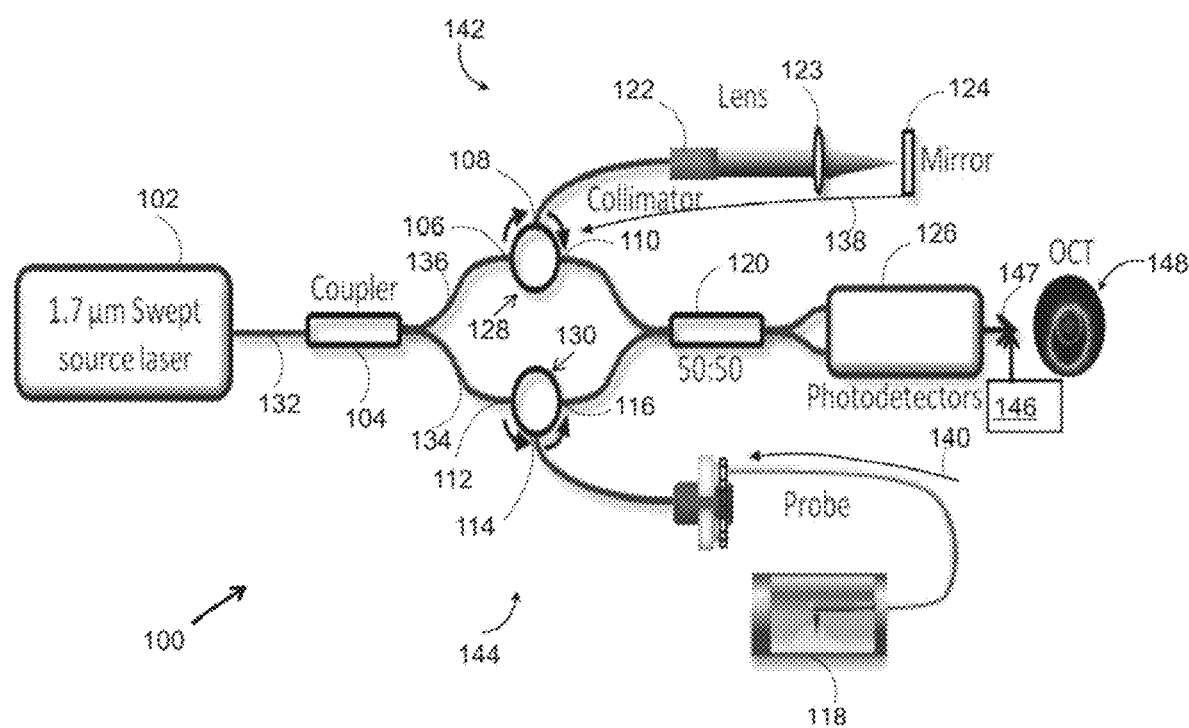
FIG. 1 shows an exemplary embodiment of the novel OCT system presented.
Figure 2:
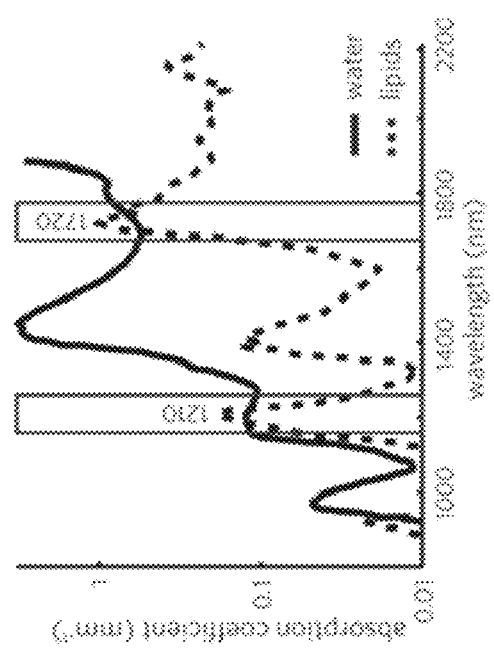
FIG. 2 shows the absorption spectrum of tissue excited by 1.2 micron and 1.7-micron wavelength signals emitted by a photoacoustic imaging system.

Following is a list of elements corresponding to a particular element referred to herein:

100 optical coherence tomography (OCT) system
102 1.7 µm swept laser source
104 first coupler
106 first port
108 second port
110 third port
112 fourth port
114 fifth port
116 sixth port
118 probe
120 second coupler
122 collimator
124 reference mirror
126 photodetector
128 first optical circulator
130 second optical circulator
132 optical source signal
134 second optical signal
136 first optical signal
138 reflected signal
140 interference signal
142 first path
144 second path
146 controller
147 signal
148 OCT image
400 intravascular OCT/US multimodal system
401 1.7 µm swept source laser
402 OCT system
404 ultrasound (US) imaging system
406 US signal
408 pulser/receiver
410 processor
412 OCT imaging signal
500 integrated intravascular OCT/Fluorescence imaging system
501 1.7 µm swept source laser
502 OCT imaging system
504 fluorescence imaging system
506 fluorescence imaging signal
508 wavelength division multiplexer (WDM)
510 double clad fiber (DCF) coupler
512 laser diode
514 filter
516 photomultiplier tube
518 OCT signal
520 processor
600 integrated intravascular OCT/Fluorescence/US imaging system
601 swept source laser
602 OCT imaging system
604 fluorescence imaging system
606 US imaging system
608 OCT signal
610 fluorescence signal
612 US imaging signal
614 processor
700 integrated intravascular OCT/OCE/US imaging system
702 OCT system
704 optical coherence elastography (OCE) system
706 US imaging system
708 US imaging signal
710 OCE imaging signal
712 OCT imaging signal
714 processor 800 integrated intravascular OCT/PAT/US imaging system
   801 swept source laser
   802 OCT system
   804 US imaging system
   806 photoacoustic(PAT) imaging system
   810 PAT signal
   812 processor
   1000 integrated microscope OCT imaging system
   1002 1.7 µm swept source laser
   1004 1.3 µm swept source laser
   1006 wavelength division multiplexer (WDM)
   1008 collimator
   1010 mirror
   1012 first beam splitter
   1014 second beam splitter
   1018 lens
   1020 sample
   1022 second photodetector
   1024 first photodetector
   1025 processor
   1026 scanner
   1028 OCT image
   1030 OCT image
   1050 integrated intravascular OCT imaging system Referring now to FIGS. 1-3, the present invention features an optical coherence tomography (OCT) system (100), comprising a swept laser source (102), effective for acquiring structural information of a tissue. In one example embodiment, the swept laser source includes a wavelength that falls in a lipid absorption spectrum. The OCT system (100) is an optical imaging modality that is used to perform high resolution cross-sectional imaging of internal microstructures in the tissue by measuring the echo time delay and magnitude of backscattered light. The 1.7 µm swept laser source (102) referenced herein is any swept source having a laser with center wavelength between 1.65-1.8 µm.

In some embodiments, the OCT system (100) may further comprise a first coupler (104), operatively connected to the swept laser source (102), configured to split an optical signal or source signal (132) emitted by the laser source (102) into a first optical signal (136) and a second optical signal (134). The first optical signal (136) may be referred to as the first portion of the optical signal, and the second optical signal (134) may be referred to as the second portion of the optical signal. Thus, the first coupler (104) splits the incoming optical signal (132) along two paths: a first path (142) and a second path (144). Herein, the first optical signal (136) traverses the first path (142) and the second optical signal (136) traverses the second optical path (144).

In an example embodiment, the first coupler (104) may include a 90:10 coupler which splits the optical signal (132) from the laser source (102). As such, the first coupler (104) transmits 90% of the optical signal (132) along the second path (144) towards a sample arm having a probe (118) and 10% of the optical signal along the first path (142) towards a reference arm having a reference mirror (124). More specifically, the second optical signal (134) may include 90% of the optical signal (132) from the laser source (102) and the first optical signal (136) may include 10% of the optical signal (132) from the laser source (102). In other example embodiments, the first coupler (104) may split the optical signal (132) in different ratios along the first and the second paths, without deviating from the scope of the present disclosure. For example, the first coupler (104) may be an 80:20 coupler that directs 80% of the optical signal (132) along the second path (144) and 10% of the optical signal (132) along the first path (142). In other examples, the first coupler (104) may be a 99:1, 90:10, 70:30 coupler or may include a coupler capable of splitting the optical signal in any desired ratio.

In further embodiments, a first optical circulator (128) may be included along the first path (142) of the OCT system (100). Specifically, the first optical circulator (128) is positioned along the first path (142) downstream of the first coupler (104). The optical circulator is a fiber-optic component that is used to separate optical signals inside an optical fiber. In one example, the first optical circulator (128) is a three-port circulator having three ports. Light entering any port of the optical circulator exits from the next port, implying that light entering a first port exits from an adjacent second port, but if some of the emitted light is reflected back to the circulator, it does not come out of the first port but instead exits from a third, different port.

The optical circulator (128) may comprise a first port (106), a second port (108) and a third port (110). After departing the first coupler (104), the first optical signal (136) enters the first port (106) of the first optical circulator (128) and exits through the second port (108) of the first optical circulator (128) for routing to a collimator (122) and a lens (123). Together, the collimator (122) and the lens (123) may focus the first optical signal (136) exiting the second port (108) onto the reference mirror (124). The aligned first signal exiting the collimator (122) and lens (123) may then be reflected back to the second port (108) by the reference mirror (124). The first optical signal (136) that is reflected back may hereafter be referred to as a reflected signal (138). The reflected signal is then directed towards the first optical circulator (128) and exits the first optical circulator (128) via the third port (110).

In additional embodiments, a second optical circulator (130) having a fourth port (112), a fifth port (114), and a sixth port (116) may be positioned along the second path (144) of the OCT system for routing the second optical signal (134) from the first coupler (104) towards the tissue. The second optical circulator (130) may be a three-port optical circulator similar to the first optical circulator (128). After exiting the first coupler (104), the second optical signal (134) may enter the fourth port (112) for transmission to the probe (118) via the fifth port (114). The probe (118) introduces the second optical signal (134) to the tissue (not shown in FIG. 1), where an interference signal (140) results from interactions between the second optical signal (134) and the tissue. The interference signal (140) then re-enters the fifth port (114) and exits through the sixth port (116). The 1.7 µm laser source allows the second optical signal to penetrate deeper into the tissue, thus generating interference signal from deep within the tissue.

Further embodiments feature a second coupler (120), operatively connected to the third port (110) of the first optical circulator (128) and the sixth port (116) of the second optical circulator (130), for coupling of the reflected optical signal (138) and the interference signal (140). More specifically, the reflected optical signal (138) and the interference signal (140) may be recombined at the second coupler (120). In one example, the second coupler (120) is a 50:50 coupler. The coupling retains information comprising the two signals, while having a 50:50 split ratio. The reflected signal (138) and the interference signal (140) are then transmitted to a photodetector (126). The photodetector (126), having a 12-bit acquisition board, may be configured to detect and record the signals and generates an output signal (147), which is subsequently processed by a processor (146) of the OCT system (100) for generating an OCT image (148). In this way, by using a higher wavelength laser source, the OCT system may generate higher contrast OCT image from deeper within the tissue.

In some examples, the first and second couplers and the first and second circulators may have the same center wavelength. As an example, the first and second couplers and the first and second circulators may have a center wavelength of around 1.7 µm. When the center wavelength of the couplers and the circulators are matched with the center wavelength of the laser source, coupling losses may be minimized. In other examples, the couplers and the circulators may have different center wavelengths. Although for 1.7 µm system, components designed for 1.7 µm will function better. However, currently many components centered around 1.7 µm is not available commercially, the inventors have demonstrated that components designed for the 1.3 µm and/or 1.5 µm can also be used to obtain high quality 1.7 µm OCT image. For example, the first and second couplers may have a center wavelength of 1.31 µm and the first and the second couplers may have a center wavelength of 1.550 µm.

In supplementary embodiments, a spectral domain OCT system may be employed utilizing a broadband light source centered at wavelengths between 1.65-1.8 µm.

The OCT system referred in this invention may be employed both as a swept source based OCT or a spectrometer based OCT system Multimodality Imaging System The present invention also features multimodality imaging systems (FIGS. 4-9), for intravascular and endoscopic OCT systems at 1.7 µm, comprising one or more integrated imaging devices. Non-limiting examples of the multimodality systems include: integrated intravascular OCT/Ultrasound ("US") imaging, intravascular OCT/Near Infrared ("NIR") imaging, intravascular OCT/US/Photoacoustic ("PAT") imaging, intravascular OCT/US/Fluorescence imaging, OCT/US/Optical Coherence Elastography ("OCE"), integrated 1.3 µm OCT and 1.7 µm OCT, and other multimodality imaging systems that include the 1.7 µm OCT system.

Figure 4:
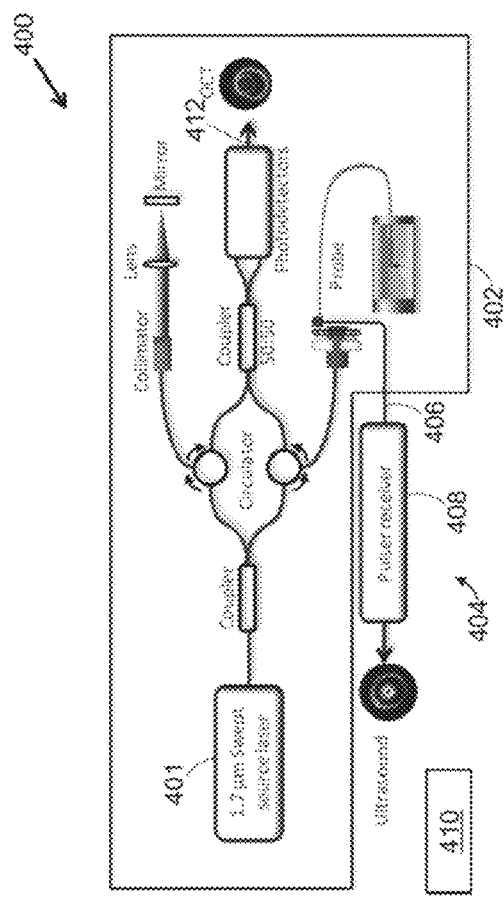
FIG. 4 shows an embodiment of the multimodal integrated intravascular OCT/US system.

FIG. 4 displays the integrated intravascular OCT/US multimodal imaging system (400). The intravascular OCT/US multimodal system (400) may include an OCT system (402) integrated with an US imaging system (404). The OCT system (402) may be one non-limiting example of the OCT system 100 described with reference to FIG. 1. A trigger signal from the swept source laser (401) of the OCT system (402) is applied as the main trigger to synchronize the US imaging system (404). For ultrasound imaging, a pulser/receiver (408) is used to generate and detect an ultrasound signal (406). A processor (410) of the system 400 may acquire OCT imaging signal (412) and US imaging signal (406) at the same time and same location. In some example embodiments, the processor (146) of the OCT system (100) may acquire OCT imaging signal (412) and US imaging signal (406) at the same time and same location.

Figure 5:
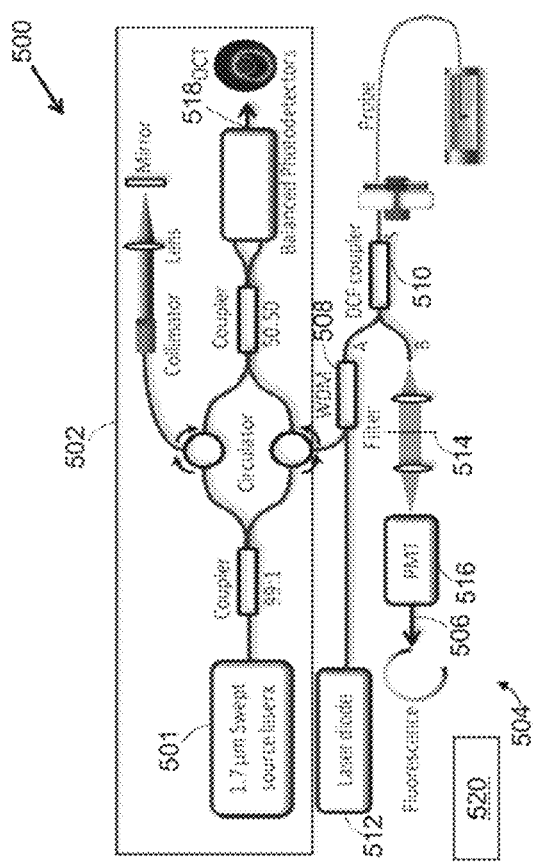
FIG. 5 shows an embodiment of the multimodal integrated intravascular OCT/Fluorescence system.

FIG. 5 displays the integrated intravascular OCT/Fluorescence imaging system (500) having an OCT imaging system (502) integrated with a fluorescence imaging system (504). The OCT imaging system (502) may be one non-limiting example of the OCT system 100 shown in FIG. 1. A trigger signal from the swept source laser (501) is applied as the main trigger to synchronize fluorescence. A wavelength division multiplexer WDM (508) may be used to combine the OCT imaging system (502) and fluorescence imaging system (504). For the fluorescence imaging system, a double clad fiber (DCF) coupler (510) may be used to collect the emission light (the DCF coupler may also supply a free space optical path to combine OCT/fluorescence). For fluorescence imaging, a laser diode (512) may be used as the excitation source, while the DCF coupler (510) may be incorporated to transmit excitation light and collect emission light. The emission light is re-routed back through the DCF coupler, then filtered by a filter (514) and detected by a photomultiplier tube (516) for fluorescence imaging. A processor (520) of the integrated intravascular OCT/Fluorescence system (500) is able to acquire OCT signal (518) and fluorescence imaging signal (506) at the same time and same location. In some example embodiments, the processor (146) of the OCT system (100) may acquire OCT signal (518) and fluorescence imaging signal (506) at the same time and same location.

Figure 6:
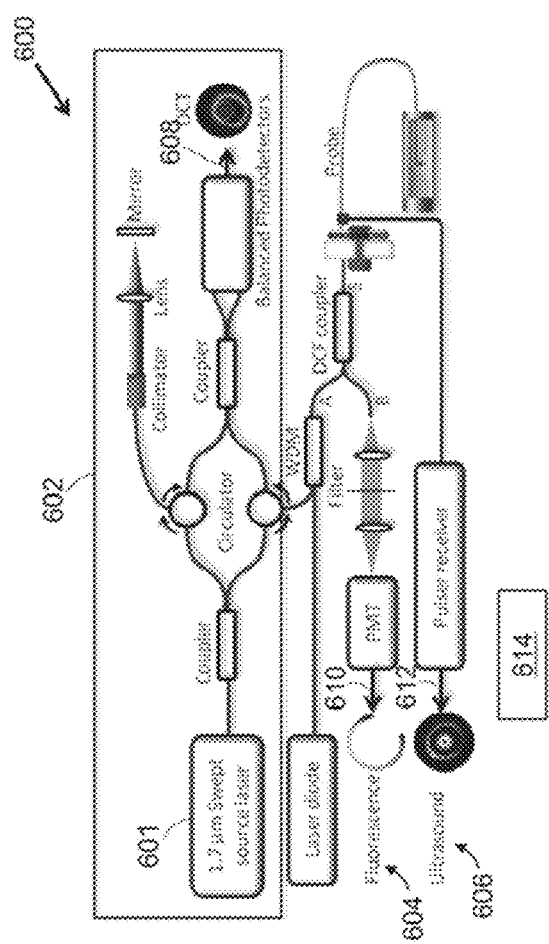
FIG. 6 shows an embodiment of the multimodal integrated intravascular OCT/Fluorescence/US system.
Figure 7:
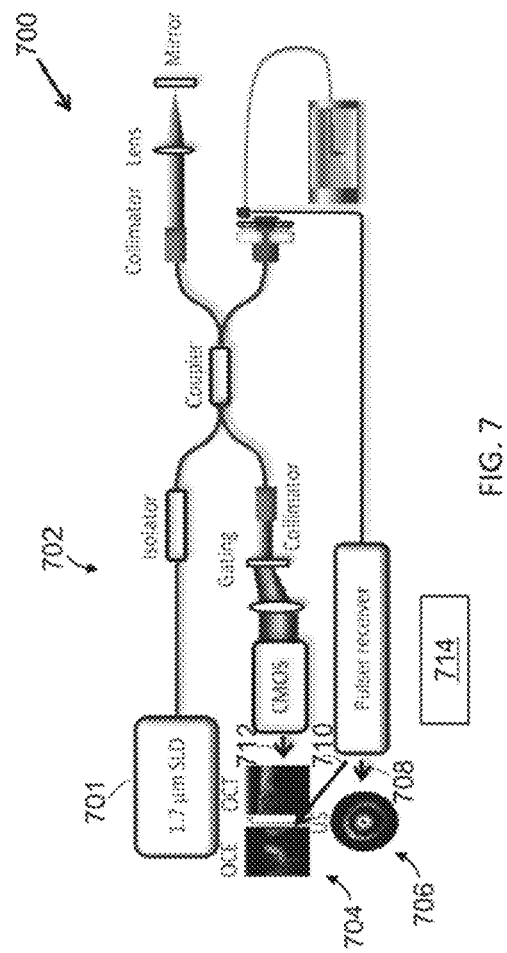
FIG. 7 shows an embodiment of the multimodal integrated intravascular OCT/OCE/US system.

FIG. 6 displays an integrated intravascular OCT/Fluorescence/US imaging system (600) having an OCT imaging system (602) integrated with a fluorescence system (604) and additionally with an ultrasound system (606). The OCT system (602) may be one non-limiting example of the OCT system (100) shown in FIG. 1, the fluorescence system (604) may be one non-limiting example of the fluorescence imaging system (504) shown in FIG. 5, and the US system (606) may be one non-limiting example of the US imaging system (404) shown in FIG. 4. Similar to the systems described herein, a trigger signal from the swept source laser (601) is applied as the main trigger to synchronize the US and fluorescence imaging. A wavelength division multiplexer (WDM) may be used to combine the OCT and fluorescence imaging systems. For the fluorescence imaging system, a double clad fiber (DCF) coupler was employed to collect the emission light (while also supplying a free space optical path to combine OCT and fluorescence). For fluorescence imaging, a laser diode may be used as the excitation source and a DCF coupler may be incorporated to transmit excitation light and collect emission light. The emission light may be routed back through DCF coupler, then filtered by a filter and detected by a photomultiplier tube for fluorescence imaging. For ultrasound imaging, a pulser/receiver may be used to generate and detect the ultrasound signal. A processor (614) integrated intravascular OCT/US/Fluorescence system is able to acquire OCT signal (608), fluorescence signal (610), and US imaging signal (612) at the same time and same location. In some example embodiments, the processor (146) of the OCT system (100) may acquire OCT signal (608), fluorescence signal (610), and US imaging signal (612) at the same time and same location. FIG. 7 displays an integrated intravascular OCT/OCE/US imaging system (700) integrated with an OCT system (702), an OCE system (704), and an US imaging system (706). A trigger signal from a broadband laser is applied as the main trigger to synchronize the US and OCE imaging. Herein, the broadband laser may be a 1.7 µm swept source laser. For ultrasound imaging, a pulser/receiver is used to generate and detect ultrasound signal (708). In addition, the pulser/receiver is also used to excite the tissue for OCE imaging and generate an OCE signal (710). Here, a delay for the pulser/receiver may be applied to separate OCE and US, or two pulsers/receivers may be applied for OCE and US imaging. A processor (714) of the integrated intravascular OCT/US/OCE system (700) is able to acquire OCT imaging signal (712), US imaging signal (708), and OCE imaging signal (710) at the same time and same location. In some example embodiments, the processor (146) of the OCT system (100)

may acquire OCT imaging signal (712), US imaging signal (708), and OCE imaging signal (710) at the same time and same location.

Figure 8:
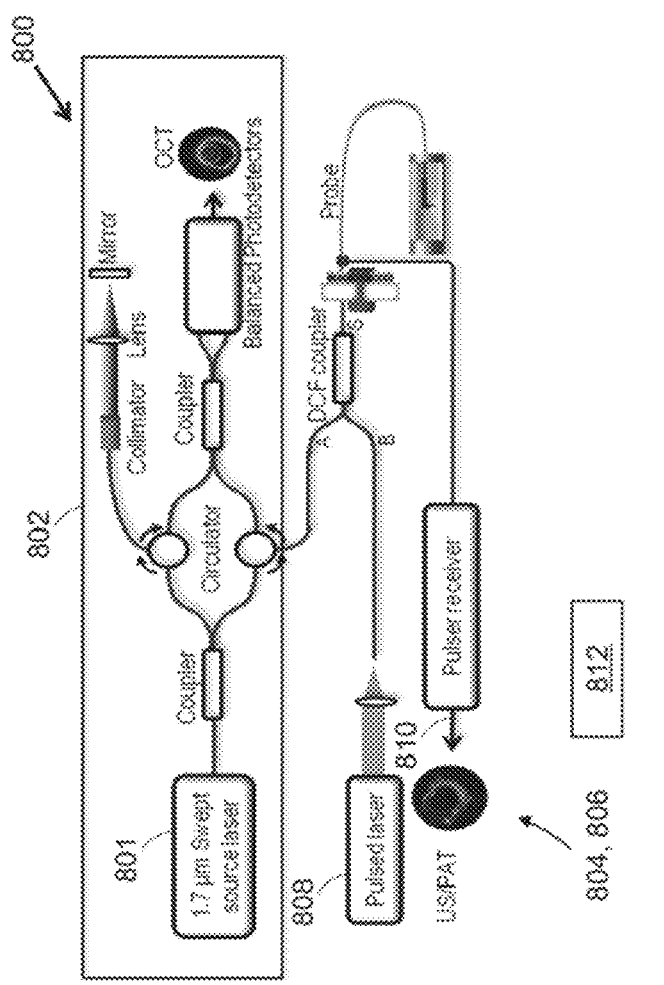
FIG. 8 shows an embodiment of the multimodal integrated intravascular OCT/PAT/US system.

FIG. 8 displays an integrated intravascular OCT/PAT/US imaging system (800) integrated with an OCT system (802), a PAT system (806), and an US imaging system (804). A trigger signal from the swept source laser (801) may be applied as the main trigger to synchronize the US and PAT imaging. For ultrasound imaging, a pulser/receiver may be used to generate and detect the ultrasound signal. A pulsed laser (808) may be used to excite tissue for the PAT signal (810), while the pulser/receiver may be used accept the PAT signal. A delay for the pulser/receiver may be applied to separate the PAT signal from the US signal, or alternately, two pulsers/receivers may be used. A processor (812) of the integrated intravascular OCT/US/PAT system (800) is able to acquire OCT, US, and PAT imaging signals at the same time and same location. In some example embodiments, the processor (146) of the OCT system (100) may acquire OCT, US, and PAT imaging signals at the same time and same location.

Figure 10A:
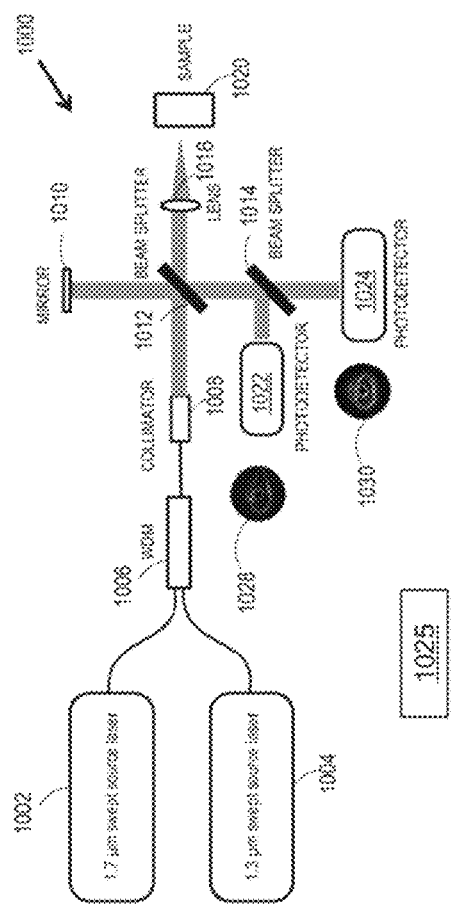
FIGS. 10A-10B show an integrated system having the 1.7 µm swept source laser and a 1.3 µm swept source laser.
Figure 10B:
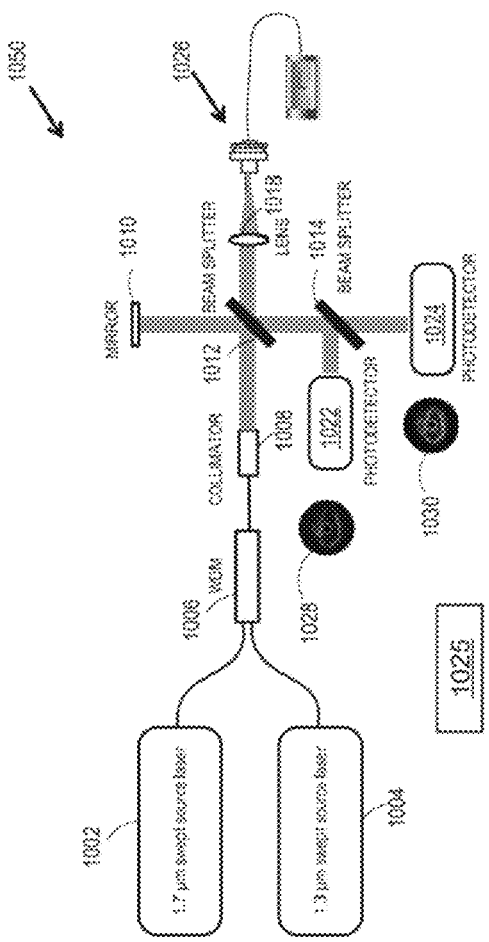

FIGS. 10 A-B display an integrated 1.3 μm OCT and 1.7 μm OCT microscopic imaging system (1000) and an integrated 1.3 μm OCT and 1.7 μm OCT intravascular imaging system (1050). The integrated systems (1000) and (1050) include a 1.7 μm swept source laser (1002) and a 1.3 μm swept source laser (1004). The optical signal from each of the swept source lasers (1002) and (1004) passes through a wavelength division multiplexer (WDM) (1006) which multiplexes the optical signals from the swept laser sources (1002 and 1004), and then collimated using a collimator (1008). The collimated optical signal (shown as a grey band in FIGS. 10 A and B) is split using a first beam splitter (1012) into two signals: one travelling towards a mirror (1010) and the other travelling towards a lens (1018) and then focused onto a sample (1020) (FIG. 10A) or towards a seamier (1026) (FIG. 10B). Herein, the first beam splitter (1012) reflects a portion of the incident signal towards the mirror (1012) and transmits the remaining portion of the incident signal towards the sample/scanner. The mirror (1010) then reflects the beam back towards the beam splitter (1012), The beam reflected from the mirror may be a reference beam. The signal reflected from the mirror (1010) is returned to the first beam splitter (1012) and is reflected towards a second beam splitter (1014). Herein, the signal from the sample/scanner is, an interference signal generated based on the interactions of the remaining portion of the incident signal and the tissue. As such, the scanner includes a probe that scans a tissue/sample. The second beam splitter (1014) de-multiplexes or separates the interference signal from the scanner/sample. Herein, the second beam splitter (1014) transmits a portion of the interference signal towards a first photodetector (1024) and reflects the remaining portion towards a second photodetector (1022). In one example embodiment, the second beam splitter (1014) may be selected such that it reflects the 1.3 μm signal and transmits the 1.7 μm signal. Each photodetector detects a portion of the signal reflected from the mirror and additionally detects interference signal from the sample/scanner centered at a particular wavelength. In this way, an OCT image (1028) may be formed based on 1.3 μm swept source laser (1004) and an OCT image (1030) may be formed based on the 1.7 μm swept source laser (1002). A trigger from one of the swept source lasers (1002 or 1004) may be applied as the main trigger to synchronize the two OCT systems. Thus, OCT images (1028) and (1030) based on 1.3 μm and 1.7 μm OCT swept source laser may be obtained at the same time and at the same location. For example, a processor 1025 of the integrated 1.3 μm OCT and 1.7 μm OCT microscope and intravascular imaging system (1000 and 1050) is able to acquire OCT images using both the 1.3 μm swept source laser and, the 1.7 μm swept source laser at the same time and same location. Based on different absorption coefficient between tissue types at two different wavelength bands, the molecular contrast can be provided through calculating the intensity ratio of two OCT images from two wavelength bands, Therefore, collagen, fibrous, fibro-fatty, fatty, calcium, cholesterol and so on can be identified for differentiating the different plaque type.

Figure 9:
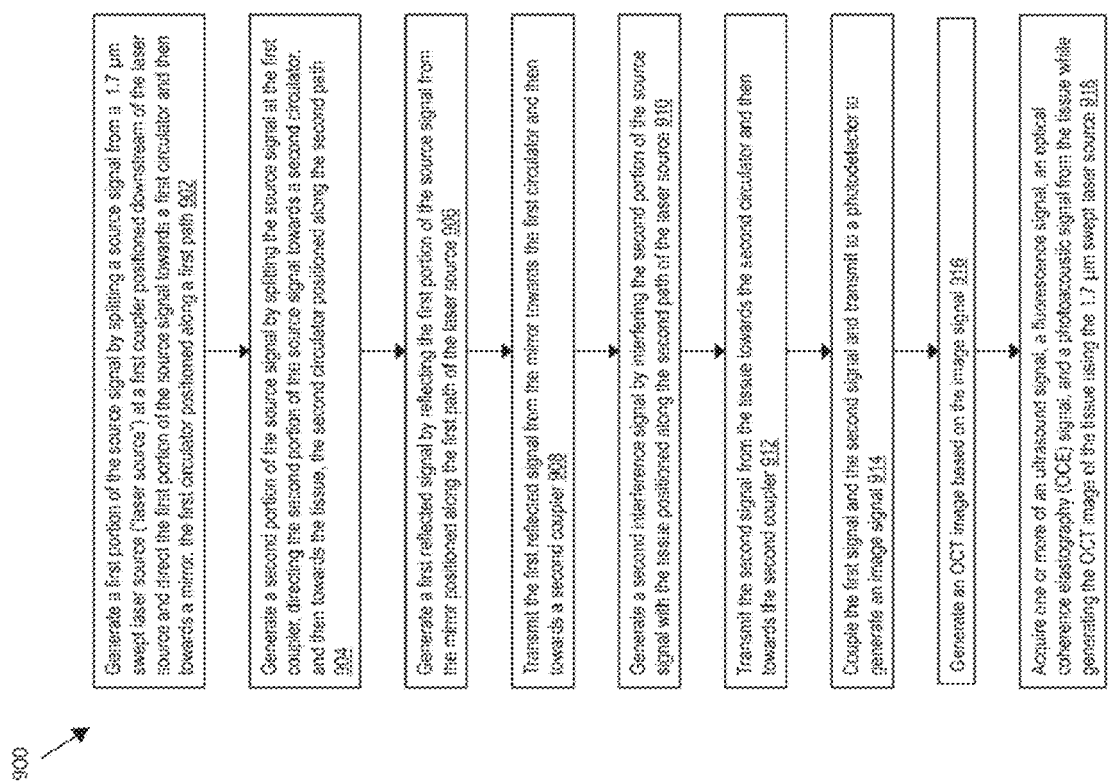
FIG. 9 shows a flowchart illustrating an example method for operating one or more of the OCT system and the multimodal integrated systems using a 1.7 µm swept laser source.

Turning now to FIG. 9, an example method 900 for operating an OCT system is shown. The OCT system may be an example of the OCT system (100) having a 1.7 μm swept laser source, as illustrated in FIG. 1 and/or a multi-modal imaging system described in FIGS. 4-8. Instructions for carrying out method 900 may be executed by a controller (such as controller 146 of FIG. 1 and/or controller 410 of FIG. 4 and/or controller 520 of FIG. 5 and/or controller 614 of FIG. 6 and/or controller 714 of FIG. 7 and/or controller 812 of FIG. 8) based on instructions stored on a memory of the controller.

Method 900 begins at 902 where a first portion of the source signal is generated by splitting a source signal from the 1.7 μm swept laser source ("laser source") at a first coupler. The first portion of the source signal is additionally directed towards a first circulator and then towards a mirror. Herein, the first circulator and the mirror are positioned along a first path of the OCT system. Method 900 proceeds to 904.

At 904, method 900 includes generating a second portion of the source signal by splitting the source signal at the first coupler, and further includes directing the second portion of the source signal towards a second circulator, and then towards the tissue.

As an example, the first coupler may be 90:10 coupler positioned downstream of the laser source. In such an example, the first portion includes 10% of the source signal and the second portion includes 90% of the source signal. Herein, the second circulator and tissue are positioned along the second path which is different from the first path of the OCT system. Method 900 proceeds to 906.

At 906, method 900 includes generating a first reflected signal by reflecting the first portion of the source signal from the mirror positioned along the first path of the laser source. Then at 908, method 900 includes transmitting the first reflected signal from the mirror towards the first circulator and then towards a second coupler.

At 910, method 900 includes generating a second interference signal by interfering the second portion of the source signal with the tissue positioned along the second path of the laser source. Then at 912, method 900 includes transmitting the second signal from the tissue towards the second circulator and then towards the second coupler. Method proceeds to 914.

At 914, method 900 includes coupling the first reflected signal transmitted from the mirror and the second interference signal transmitted from the tissue at the second coupler. The coupled signal is then transmitted to a photodetector. The photodetector generates an image signal based on the first reflected signal and the second interference signal. Method 900 proceeds to 916.

At 916, method 900 includes generating an OCT image based on the image signal generated at 914. If the OCT system is a multimodality imaging system (FIGS. 4-8), then at 918, method 900 includes acquiring one or more of an ultrasound signal, a fluorescence signal, an optical coherence elastography (OCE) signal, and a photoacoustic signal from the tissue while simultaneously generating the OCT image of the tissue using the 1.7 µm swept laser source.

Compared with the conventional OCT systems which use shorter wavelength laser source, the longer wavelength laser source of the present disclosure offers higher sensitivity, deeper tissue penetration, higher signal to noise ratio, and increased sensitivity, which makes the OCT system of the present disclosure a better tool for characterization of atherosclerosis as described below.

Results and Conclusions

A new contrast mechanism based on the overtone absorption of C—H bonds excited by wavelengths of 1.2 µm or 1.7 µm provides lipid-specific contrast, and has been used for photoacoustic imaging for identifying lipid-laden plaque, as shown in FIG. 2. This contrast mechanism was applied in the present OCT system for identifying atherosclerotic plaque. The system was able to acquire structural information of tissue with a high resolution, a large penetration depth and high sensitivity for lipid composition. The high resolution contributes to the identification of the thin fibrous cap. The large penetration depth and high sensitivity could be used for identifying the lipid pool.

Figure 3B:
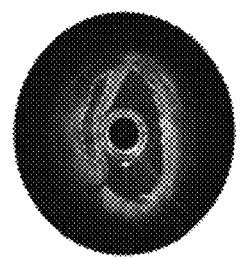
FIGS. 3A-3D show images of a human coronary artery acquired by the present OCT system.
Figure 3D:
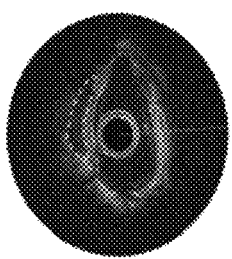
Figure 3A:
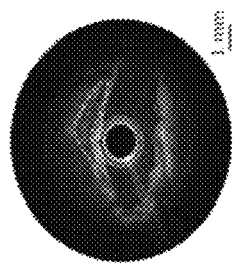
Figure 3C:
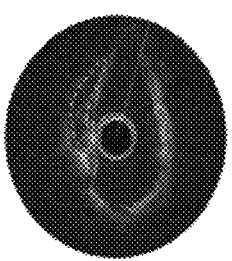

To evaluate the performance of the present OCT system, imaging from a human coronary artery was performed. In addition, the same coronary artery was imaged using conventional OCT system as a comparison. Representative OCT images are shown in FIG. 3. FIGS. 3A and 3B show OCT images obtained by 1.7 µm OCT device in water and air, respectively. FIGS. 3C-D show OCT images obtained by 1.3 µm OCT device in water and air, respectively. Comparing FIGS. 3A and 3B, it can be seen that although absorption of water decreases the SNR of OCT images, the large lipid pool is still clearly identifiable in the images produced by the present imaging system. Comparing FIG. 3A with 3C and 3B with 3D, the lipid pool is easily identified by 1.7 µm OCT device.

Figure 11B:
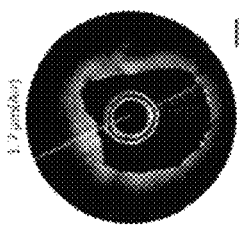
FIGS. 11A-11D show images of a healthy human coronary artery, imaged using a 1.3 µm IVOCT system and the 1.7 µm IVOCT system
Figure 11D:
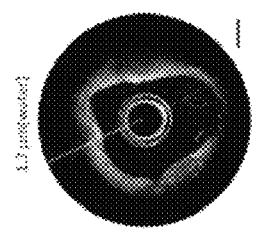
Figure 11A:
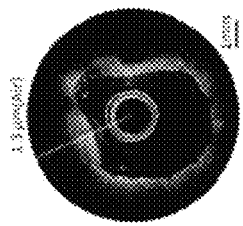
Figure 11C:
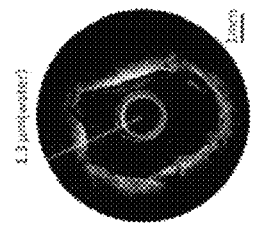
Figure 11E:
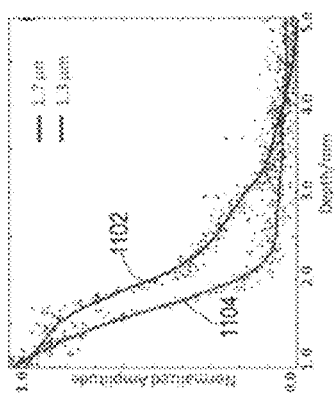
FIGS. 11E-11F show quantitative analysis of penetration depth for the two IVOCT systems in air and water. Scale bars are 1 mm.
Figure 11F:
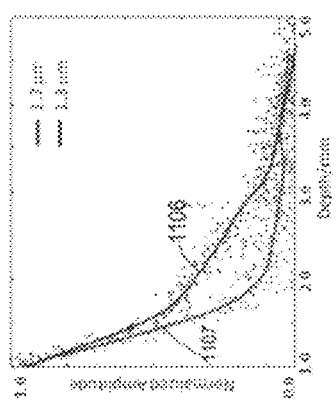

To verify the capability of large penetration depth with the 1.7 µm IVOCT system, a healthy human coronary artery was imaged with both the 1.3 µm IVOCT system and the 1.7 µm IVOCT system. Herein, FIGS. 11A and 11C show IVOCT images obtained by the 1.3 µm IVOCT system in air and water, respectively and FIGS. 11B and 11D show IVOCT images obtained by the 1.7 µm IVOCT system in water and air, respectively. Comparing FIGS. 11A and 11B, 11C and 11D, it can be seen that more information was obtained along the axial direction with the 1.7 µm IVOCT system. FIGS. 11E and 11F are the quantitative analysis of penetration depth for the two IVOCT systems in air and water. In FIGS. 11E and F, normalized amplitude is shown along the Y-axis, and depth/mm is shown along X-axis. As shown in FIG. 11E, larger penetration depth is achievable in air with the 1.7 µm IVOCT system (plot 1102) as opposed to the penetration depth achievable in air with the 1.3 µm IVOCT system (plot 1104). Likewise, larger penetration depth is also achievable in water with the 1.7 µm IVOCT system (plot 1106) as opposed to the penetration depth achievable in water with the 1.3 µm IVOCT system (plot 1107).

Figure 12:
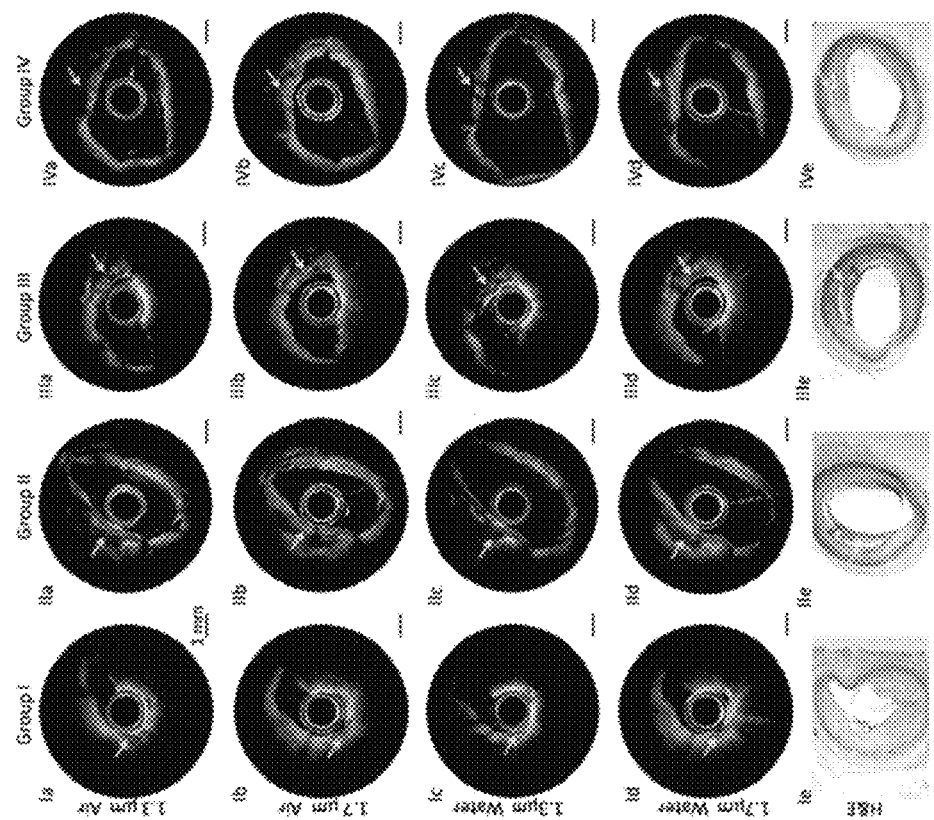
FIG. 12 shows images of atherosclerotic coronary arteries, imaged by using the 1.3 µm IVOCT system and the 1.7 µm IVOCT system.

To demonstrate the capability of differentiating plaque from normal tissue, the atherosclerotic coronary arteries were imaged by using the two IVOCT systems, the images are shown in FIG. 12. Groups (I-IV) are IVOCT images at different artery sites with different pathological features. FIG. 12(*a-d*) were obtained at similar sites by the 1.3 µm and 1.7 µm IVOCT systems in both air and water. FIG. 12 (Ie-IVe) are corresponding hematoxylin and eosin (H&E) histology for each group. For group I, a low-density signal region (denoted by the yellow arrow) can be found in FIG. 12 (Ia-Ie), which indicates the existence of calcium plaque. The classification of plaque type is validated by the corresponding histology images, which matches the four IVOCT images well. For groups II and IV, a large low-density signal region was also found, which indicates the existence of thick-cap (>65 µm) fibroatheroma (ThCFA). The corresponding H&E histology [FIG. 12 (II e) and (IVe)] all verified the results. For group III (a-d), a thin fibrous cap and a large low-density signal region behind the thin fibrous cap were found, indicating thin-cap (<65 µm) fibroatheroma (TCFA). FIG. 12 (IIIe) histology verified these results. Comparing the IVOCT images of the 1.3 µm IVOCT system and the 1.7 µm IVOCT system, it is clearly seen that the 1.7 µm IVOCT system images have a larger penetration depth compared to the 1.3 µm IVOCT system images which demonstrates the capability of the 1.7 µm IVOCT system to visualize the whole plaque. Analyzing the results in water and air, it is noted that the absorption of water is almost negligible for the atherosclerotic coronary artery due to the small lumen. These IVOCT images and H&E histology illustrate the capability of the 1.7 µm system to identify the plaque with large imaging depth and high sensitivity.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

REFERENCES

E. Falk, P. K. Shah, and V. Fuster, "Coronary Plaque Disruption," Circulation 92, 657-671 (1995).

A. V. Finn, M. Nakano, J. Narula, F. D. Kolodgie, and R. Virmani, "Concept of Vulnerable/Unstable Plaque," ArteriosclThrom Vas 30, 1282-1292 (2010). [doi: 10.1161/ATVBAHA.108.179739].

M. Naghavi, P. Libby, E. Falk, S. W. Casscells, S. Litovsky, J. Rumberger, J. J. Badimon, C. Stefanadis, P. Moreno, G. Pasterkamp, Z. Fayad, P. H. Stone, S. Waxman, P. Raggi, M. Madjid, A. Zarrabi, A. Burke, C. Yuan, P. J. Fitzgerald, D. S. Siscovick, C. L. de Korte, M. Aikawa, K. E. Airaksinen, G. Assmann, C. R. Becker, J. H. Chesebro, A. Farb, Z. S. Galis, C. Jackson, I. K. Jang, W. Koenig, R. A. Lodder, K. March, J. Demirovic, M. Navab, S. G. Priori, M. D. Rekhter, R. Bahr, S. M. Grundy, R. Mehran, A. Colombo, E. Boerwinkle, C. Ballantyne, W. Insull, Jr., R. S. Schwartz, R. Vogel, P. W. Serruys, G. K. Hansson, D. P. Faxon, S. Kaul, H. Drexler, P. Greenland, J. E. Muller, R. Virmani, P. M. Ridker, D. P. Zipes, P. K. Shah, and J. T. Willerson, "From vulnerable plaque to vulnerable patient: a call for new definitions and risk assessment strategies: Part II," Circulation 108(15), 1772-1778 (2003).

J. A. Ambrose, M. A. Tannenbaµm, Alexopoulos, C. E. Hjemdahl-Monsen, J. Leavy, M. Weiss, S. Borrico, R. Gorlin, V. Fuster, "Angiographic progression of coronary artery disease and the development of myocardial infarction. J Am Coll Cardiol," 1988; 12:56-62.

Yabushita H, Boµma B E, Houser S L, Aretz H T, Jang I K, Schlendorf K H, Kauffman C R, Shishkov M, Kang D H, Halpern E, Tearney G J. Characterization of hµman atherosclerosis by optical coherence tomography. Circulation. 2002; 106: 1640-1645.

G. J. Tearney, H. Yabushita, S. L. Houser, H. T. Aretz, I. K. Jang, K. H. Schlendorf, C. R. Kauffman, M. Shishkov, E. F. Halpern, and B. E. Boµma, "Quantification of macrophage content in atherosclerotic plaques byoptical coherence tomography," Circulation 107(1), 113-119 (2003).

J Fujimoto, S Boppart, G Tearney, B Boµma, C Pitris, and M Brezinski, "High resolution in vivo intra-arterial imaging with optical coherence tomography," Heart. 1999; 82(2): 128-133.

Tearney G J, Waxman S, Shishkov M, Vakoc B J, Suter M J, Freilich M I, Desjardins A E, Oh W-Y, Bartlett L A, Rosenberg M, Boµma B E. Three-dimensional coronary artery microscopy by intracoronary optical frequency domain imaging. J Am Coll Cardiollmg. 2008; 1:752-61.

M. Abran, B. E. Stähli, N. Merlet, T. Mihalache-Avram, M. Mecteau, E. Rhêaµme, D. Busseuil, J. C. Tardif, F. Lesage, "Validating a bimodal intravascular ultrasound (IVUS) and near-infrared fluorescence (NIRF) catheter for atherosclerotic plaque detection in rabbits," Biomed Opt Express. 2015 Sep. 14; 6(10):3989-99. J. Bec, D.

What is claimed is:

1. An optical coherence tomography ("OCT") system (100) effective for acquiring structural and chemical information of a tissue, the system (100) comprising:
   a. the tissue, where in the tissue is not altered by a fluorescent dye or pigment;
   b. only one laser source (102) having a wavelength in a lipid absorption spectrum at 1.7 µm for providing molecular contrast of the tissue;
   c. a first coupler (104), operatively connected to the laser source (102), configured to split an optical signal (132) emitted by the laser source (102) into a first optical signal (136) and a second optical signal (134);
   d. a first optical circulator (128) operatively connected to the first coupler (104) and having a first port (106), a second port (108) and a third port (110), wherein the first optical signal (136) enters the first port (106) and exits through the second port (108), whereupon exiting the second port (108), the first optical signal is routed to a collimator (122) before being reflected back to the second port (108) via a reference mirror (124), wherein the first optical signal (136) then exits the first optical circulator (128) via the third port (110);
   e. a second optical circulator (DO) operatively connected to the first coupler (104) having a fourth port (112), a fifth port (114), and a sixth port (116), wherein the second optical signal enters the fourth port (112) and exits the fifth port (114) whereupon exiting the fifth port (114), the second optical signal (134) is routed to a probe (118) operatively connected to the tissue, wherein an interference signal (140) results from interactions between the second optical signal and the tissue; wherein the interference signal (140) re-enters the fifth port (114) to exit through the sixth port (116), wherein the probe (118) is disposed in a plurality of bodily fluids;
   a second coupler (120) operatively connected to the third port (110) and the sixth port (116), wherein the first optical signal (136) and the interference signal comprise input to the second coupler (120), wherein the second coupler (120) splits the first optical signal and the interference signal in a 50:50 split ratio; and
   g. a photodetector (126) having a data acquisition board, configured to detect and record an output of the second coupler (120), centered at 1.7 µm,
   wherein the output of the second coupler (120) contains structural information describing the tissue, wherein an output (147) of the photodetector (126) is transmitted to an OCT device for imaging.

2. The system of claim 1, wherein the laser source (102) comprises a broadband light source centered at 1.7 µm, and wherein the OCT system further comprises a spectral meter at a detection arm of the OCT system.

3. The system of claim 1, wherein one or more imaging systems or combinations thereof are integrated into the OCT system to produce a multimodality imaging system, the one or more imaging systems comprising an ultrasound ("US") imaging system (404), a fluorescence imaging system (504), an optical coherence elastography (OCE) imaging system (704), a photoacoustic (PAT) imaging system (806), near-infrared spectroscopy imaging system, a fractional flow reserve (FFR) measurement system, a 1.3 µm swept source laser (1004) system, or combinations thereof.

4. A method of producing an optical coherence tomography (OCT) image, the method comprising:
   a. providing an OCT system according to claim 1;
   b. generating (906) a first signal from only one source signal of the laser source (102) by reflecting a first portion of the source signal from a mirror positioned along a first path of the laser source;
   c. generating (910) a second signal by interfering a second portion of the source signal with a tissue positioned along a second path of the laser source;
   d. coupling (914) the first signal and the second signal to generate an image signal; and
   e. generating (916) an optical coherence tomography (OCT) image based on the image signal, wherein the OCT image generated by coupling the first signal and the second signal contains structural information describing the tissue.

5. The method of claim 4, comprising generating the first portion of the source signal by splitting (902) the source signal at a first coupler positioned downstream of the laser source, directing (902) the first portion of the source signal towards a first circulator and then towards the mirror, the first circulator positioned along the first path, and wherein the laser source (102) includes a laser with center wavelength at 1.7 µm.

6. The method of claim 5, comprising generating (904) the second portion of the source signal by splitting the source signal at the first coupler, directing the second portion of the source signal towards a second circulator, and then towards the tissue, the second circulator positioned along the second path.

7. The method of claim 6, further comprising:
   transmitting (908) the first signal from the mirror towards the first circulator and then towards a second coupler; and
   transmitting (912) the second signal from the tissue towards the second circulator and then towards the second coupler.

8. The method of claim 7, wherein the first coupler is a 90:10 coupler and the second coupler is a 50:50 coupler, and each of the first circulator and the second circulator is a three-port circulator each having three ports.

9. The method of claim 4, further comprising acquiring (918) one or more of an ultrasound signal, a fluorescence signal, an optical coherence elastography (OCE) signal, and a photoacoustic signal from the tissue while generating the OCT image of the tissue using the laser source.

10. The system of claim 1, wherein the laser source (102) comprises a swept light source centered at 1.7 μm.

* * * * *